(12) United States Patent
Gifford et al.

(10) Patent No.: US 10,378,883 B2
(45) Date of Patent: Aug. 13, 2019

(54) FORCE SENSING IN A DISTAL REGION OF AN INSTRUMENT INCLUDING SINGLE-CORE OR MULTI-CORE OPTICAL FIBER

(71) Applicant: INTUITIVE SURGICAL OPERATIONS, INC., Sunnyvale, CA (US)

(72) Inventors: Dawn K. Gifford, Blacksburg, VA (US); Federico Barbagli, San Francisco, CA (US); Samuel Y. Chang, Mountain View, CA (US); Anoop B. Kowshik, Saratoga, CA (US); Oliver J. Wagner, Mountain View, CA (US); Michael D. Paris, San Francisco, CA (US); Mark E. Froggatt, Blacksburg, VA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 15/572,135

(22) PCT Filed: May 12, 2016

(86) PCT No.: PCT/US2016/032051
§ 371 (c)(1),
(2) Date: Nov. 6, 2017

(87) PCT Pub. No.: WO2016/186951
PCT Pub. Date: Nov. 24, 2016

(65) Prior Publication Data
US 2018/0128599 A1    May 10, 2018

Related U.S. Application Data

(60) Provisional application No. 62/162,062, filed on May 15, 2015.

(51) Int. Cl.
*G02B 6/02* (2006.01)
*G01B 11/16* (2006.01)
(Continued)

(52) U.S. Cl.
CPC .......... *G01B 11/16* (2013.01); *A61B 1/00096* (2013.01); *A61B 1/00165* (2013.01);
(Continued)

(58) Field of Classification Search
CPC ............... G01D 5/353; G01D 5/35306; G01D 5/35312; G01D 5/35319; G01D 5/35325;
(Continued)

(56) References Cited

U.S. PATENT DOCUMENTS 7,781,724 B2   8/2010   Childers et al.
8,567,265 B2   10/2013  Aeby et al.
(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
(Continued)

*Primary Examiner* — Jonathan M Hansen
(74) *Attorney, Agent, or Firm* — Schwegman Lundberg & Woessner, P.A.

(57) ABSTRACT

An optical force sensor along with an optical processing apparatus and method are disclosed. The optical force sensor includes an optical fiber, a core included in the optical fiber, an instrument including the optical fiber, the instrument having a distal region, and a tubular structure encasing an end of the optical fiber and secured to the first conduit at the distal region of the instrument. When an optical interferometric system is coupled to the optical fiber, it processes reflected light from a portion of the core included within the
(Continued)

tubular structure that does not include Bragg gratings to produce a measurement of a force present at the distal region of the instrument.

20 Claims, 9 Drawing Sheets

(51) Int. Cl.
*G01L 1/24* (2006.01)
*G02B 23/26* (2006.01)
*A61B 1/00* (2006.01)
*G02B 6/34* (2006.01)
*G02B 6/00* (2006.01)

(52) U.S. Cl.
CPC .................. *G01L 1/24* (2013.01); *G02B 6/00* (2013.01); *G02B 6/02* (2013.01); *G02B 6/022* (2013.01); *G02B 6/02042* (2013.01); *G02B 6/34* (2013.01); *G02B 23/26* (2013.01)

(58) Field of Classification Search
CPC ........... G01D 5/35329; G01D 5/35332; G01D 5/3537; G02B 6/00; G02B 6/02; G02B 6/02052

See application file for complete search history.

(56) References Cited

U.S. PATENT DOCUMENTS

| 8,622,935 | B1* | 1/2014 | Leo ..................... A61B 5/6843 600/587 |
| 8,773,650 | B2 | 7/2014 | Froggatt et al. |
| 2005/0050962 | A1* | 3/2005 | Zerwekh ............ G01K 11/3206 73/800 |
| 2007/0165238 | A1* | 7/2007 | Boyd ..................... G01L 1/242 356/478 |
| 2011/0224684 | A1 | 9/2011 | Larkin et al. |
| 2011/0310378 | A1 | 12/2011 | Froggatt et al. |
| 2012/0134621 | A1 | 5/2012 | Haslinger |
| 2013/0317372 | A1* | 11/2013 | Eberle ................ A61B 5/02154 600/478 |
| 2015/0077736 | A1* | 3/2015 | Reinsch ............ G01D 5/35312 356/32 |

OTHER PUBLICATIONS

International Search Report and Written Opinion for Application No. PCT/US2016/032051, dated Aug. 22, 2016, 10 pages.

* cited by examiner

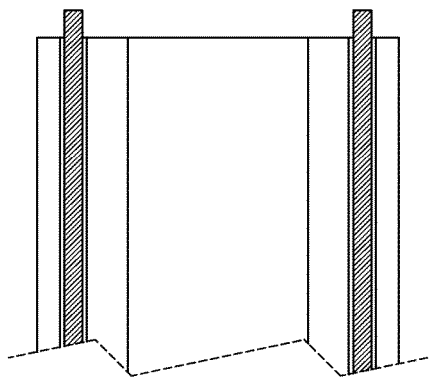
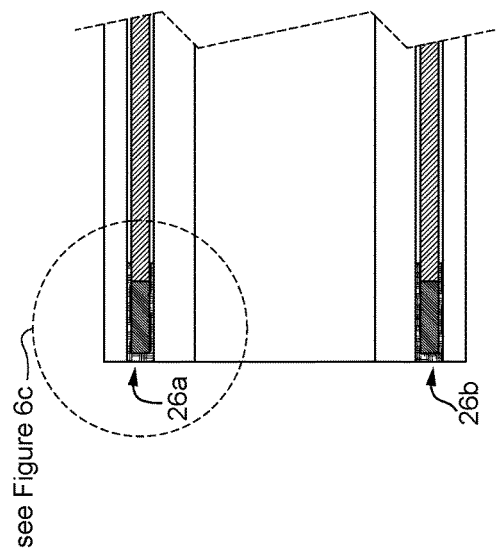
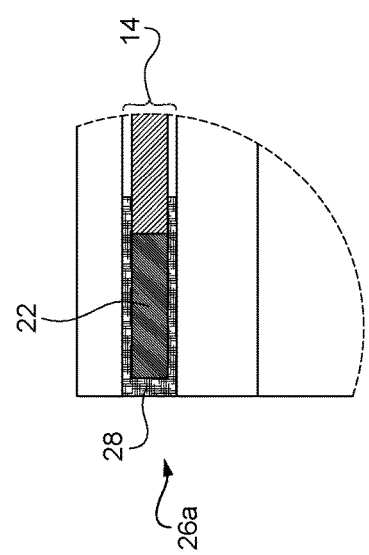
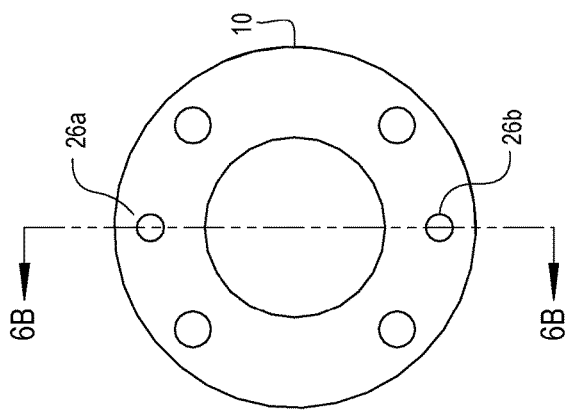
Figure 6B
Figure 6C
Figure 6A

FORCE SENSING IN A DISTAL REGION OF AN INSTRUMENT INCLUDING SINGLE-CORE OR MULTI-CORE OPTICAL FIBER

RELATED APPLICATIONS

This application is the U.S. national phase of International Application No. PCT/US2016/032051 filed May 12, 2016 which designated the U.S. and claims priority to and the benefit of the filing date of U.S. Provisional Patent Application 62/162,062, entitled "FORCE SENSING IN A DISTAL REGION OF AN INSTRUMENT INCLUDING SINGLE-CORE OR MULTI-CORE OPTICAL FIBER," filed May 15, 2015, the entire contents of each of which are hereby incorporated by reference.

TECHNICAL FIELD

The technology relates to instruments that use optical fiber sensing.

INTRODUCTION

Optical strain sensing is a technology useful for measuring physical deformation of a waveguide caused by, for example, the change in tension, compression, or temperature of an optical fiber. This can be done with a standard, single core optical fiber or with a multi-core optical fiber. A multi-core optical fiber includes multiple independent waveguides or cores embedded within a single fiber. A continuous measure of strain along the length of a core can be derived by interpreting the optical response of the core using swept wavelength inteferometery. With knowledge of the relative positions of the cores along the length of the fiber, these independent strain signals for each of the cores may be combined to gain a measure of the strain profile applied to the multi-core optical fiber. The strain profile of the fiber refers to the measure of applied bend strain, twist strain, and/or axial strain along the length of the fiber at a high (e.g., less than 50 micrometers) sample resolution. In a technique known as optical position and/or shape sensing, detailed for example in commonly-assigned U.S. Pat. No. 8,773,650 to Froggatt et al, which is incorporated herein by reference, this strain profile information can be used to reconstruct the three dimensional position of the fiber.

SUMMARY

The inventors realized that it would be desirable to be able to determine one or more forces present at the distal region of an instrument and that optical strain sensing technology could be used to determine such forces.

Example embodiments include an optical force sensor that includes an optical fiber, a core included in the optical fiber, an instrument including the optical fiber, the instrument having a distal region, and a tubular structure encasing an end of the optical fiber and secured at the distal region of the instrument. The optical fiber is configured for connection to an optical interferometric system which processes reflected light from a portion of the core included within the tubular structure that does not include Bragg gratings to produce a measurement of a force present at the distal region of the instrument.

In a non-limiting example implementation, the optical fiber is tapered within the tubular structure and is secured within the tubular structure by an epoxy index-matched to the optical fiber. The epoxy transfers strain from the distal region of the instrument to the optical fiber.

The tubular structure may be made, for example, of metal, glass, or polymer. In a non-limiting example implementation, the tubular structure completely surrounds the end of the optical fiber.

The tubular structure may be secured at the end of the optical fiber using a mechanical attachment, an adhesive attachment, or a flame spray attachment.

In a non-limiting example implementation, the instrument includes a first conduit into which the optical fiber is inserted. The tubular structure is bonded to the first conduit at a bonded region that extends as far as the tubular structure. The core includes Bragg gratings except on a portion of the core defined by the bonded region.

In another non-limiting example implementation, the instrument includes a first conduit into which the optical fiber is inserted. The tubular structure is bonded to the first conduit at the end of the optical fiber at a bonded region that extends beyond the tubular structure and secures the optical fiber to the first conduit. The core includes Bragg gratings that extend into the bonded region.

In another non-limiting example implementation, the optical fiber includes multiple cores.

In another non-limiting example implementation, the instrument includes a first conduit into which the optical fiber is inserted and a second conduit containing another optical fiber encased in a similar tubular structure. The optical interferometric system processes reflected light from portions of the core contained within the tubular structures of the respective optical fibers that do not include Bragg gratings to produce a measurement of forces present on the respective tubular structures.

Further example embodiments include an optical processing apparatus having an optical fiber, a core included in the optical fiber, an instrument including the optical fiber, the instrument having a distal region, a tubular structure encasing an end of the optical fiber and secured at the distal region of the instrument, and an optical interferometric system coupled to the optical fiber. The optical interferometric system is configured to process reflected light from a portion of the core included within the tubular structure that does not include Bragg gratings to produce a measurement of a force present at the distal region of the instrument.

In a non-limiting example implementation, the optical fiber is tapered within the tubular structure and is secured within the tubular structure by an epoxy index-matched to the optical fiber, the epoxy transferring strain from the instrument to the optical fiber. In an example application, the optical interferometric system is configured to determine strain present on the distal region of the instrument and to determine the force based on the determined strain. Furthermore, the optical interferometric system may be configured to determine the strain present on the distal region of the instrument based on a first light reflection from a distal end of the optical fiber and on a second light reflection from a distal end surface of the epoxy. The first and second reflections form an interference pattern with a sinusoidal oscillation as a function of optical frequency. In this example, the optical interferometric system is configured to measure a change in a period of the sinusoidal oscillation to determine the strain present on the distal region of the instrument.

In another non-limiting example implementation, the optical interferometric system is configured to detect a scatter pattern within the tubular structure, compare the detected scatter pattern to a reference scatter pattern to determine a difference, and determine the force based on the difference.

In another non-limiting example implementation, the instrument includes a first conduit into which the optical fiber is inserted and a second conduit into which a second optical fiber is inserted. A second tubular structure encases an end of the second optical fiber located at the distal region and is secured within the second tubular structure by an epoxy index-matched to the optical fiber. The epoxy transfers strain from the first and second conduits to the optical fiber. The optical interferometric system is configured to process reflected light from a portion of respective cores in the first and second optical fibers that do not include Bragg gratings to produce a measurement of multiple forces present on the distal region of the instrument.

Further example embodiments include an optical processing method using an optical fiber including a core attached to an instrument having a distal region. A tubular structure encases an end of the optical fiber and is secured at the distal region of the instrument. The method includes processing, using by an optical interferometric system, reflected light from a portion of the core included within the tubular structure that does not include Bragg gratings to produce a measurement of a force present at the distal region of the instrument. The method may further include determining strain present on the distal region of the instrument and determining the force based on the determined strain.

In a non-limiting example implementation, the optical interferometric system determines the strain present on the distal region of the instrument based on a first light reflection from a distal end of the optical fiber and on a second light reflection from a distal end surface of the epoxy. The first and second light reflections form an interference pattern with a sinusoidal oscillation as a function of optical frequency. A change in a period of the sinusoidal oscillation is measured to determine the strain present on the distal region of the instrument.

In a non-limiting example implementation, a scatter pattern within the tubular structure is detected and compared to a reference scatter pattern to determine a difference. The force is determined based on the difference.

BRIEF DESCRIPTION OF THE DRAWINGS

FIGS. 6A-6C show various views of the end of the instrument shown in FIG. 5;

DETAILED DESCRIPTION

Figure 1:
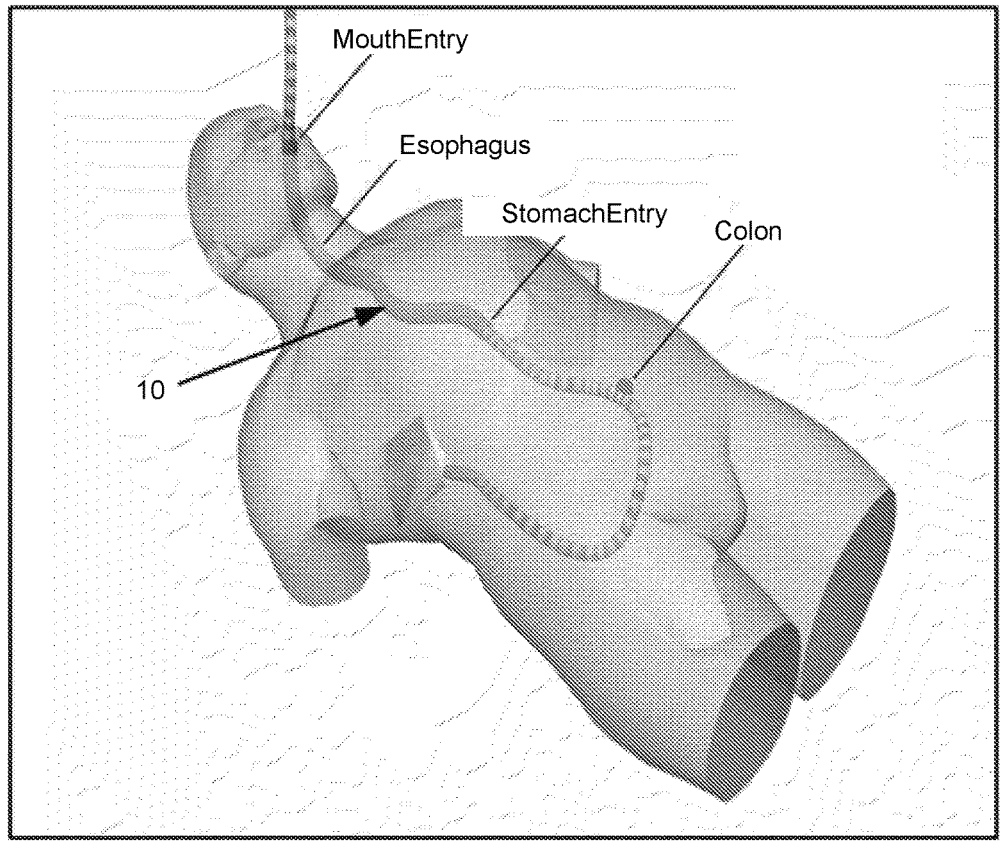
FIG. 1 shows a non-limiting example medical application of an instrument.

The following description sets forth specific details, such as particular embodiments for purposes of explanation and not limitation. But it will be appreciated by one skilled in the art that other embodiments may be employed apart from these specific details. In some instances, detailed descriptions of well known methods, interfaces, circuits, and devices are omitted so as not to obscure the description with unnecessary detail. Individual blocks are shown in the figures corresponding to various nodes. Those skilled in the art will appreciate that the functions of those blocks may be implemented using individual hardware circuits, using software programs and data in conjunction with a suitably programmed digital microprocessor or general purpose computer, and/or using applications specific integrated circuitry (ASIC), and/or using one or more digital signal processors (DSPs). Software program instructions and data may be stored on a non-transitory, computer-readable storage medium, and when the instructions are executed by a computer or other suitable processor control, the computer or processor performs the functions associated with those instructions.

Thus, for example, it will be appreciated by those skilled in the art that diagrams herein can represent conceptual views of structures and functional units. It will be appreciated that a flow chart represents processes which may be substantially represented in computer-readable medium and so executed by a computer or processor, whether or not such computer or processor is explicitly shown.

The functions of the various illustrated elements may be provided through the use of hardware such as circuit hardware and/or hardware capable of executing software in the form of coded instructions stored on computer-readable medium. Thus, such functions and illustrated functional blocks are to be understood as being either hardware-implemented and/or computer-implemented, and thus machine-implemented.

In terms of hardware implementation, functional data processing blocks may include or encompass, without limitation, a digital signal processor (DSP) hardware, a reduced instruction set processor, hardware (e.g., digital or analog) circuitry including but not limited to application specific integrated circuit(s) (ASIC) and/or field programmable gate array(s) (FPGA(s)), and (where appropriate) state machines capable of performing such functions.

In terms of computer implementation, a computer is generally understood to comprise one or more processors or one or more controllers, and the terms computer, processor, and controller may be employed interchangeably. When provided by a computer, processor, or controller, the functions may be provided by a single dedicated computer or processor or controller, by a single shared computer or processor or controller, or by a plurality of individual computers or processors or controllers, some of which may be shared or distributed. Moreover, the term "processor" or "controller" also refers to other hardware capable of performing such functions and/or executing software, such as the example hardware recited above.

In one example application, multicore optical fiber can be used to sense the shape of robotic medical instruments. FIG. 1 shows a non-limiting example medical application of an instrument 10 that include an optical fiber-based sensor. In these and other applications, it is often desirable to provide shape sensing as close as possible to the distal region of the instrument. It is also desirable to terminate the fiber at the instrument distal region to suppress any strong back reflection by angle cleaving or tapering the end of the fiber. A strong reflection at the end of a fiber at a cleaved air/glass interface can overwhelm other, smaller reflections in the fiber such as Rayleigh backscatter, fiber Bragg gratings, or other minute reflections used for sensing strain. Therefore, it is often necessary to terminate the fiber in some way that suppresses the natural Fresnel reflection at the air/glass interface.

Figure 2:
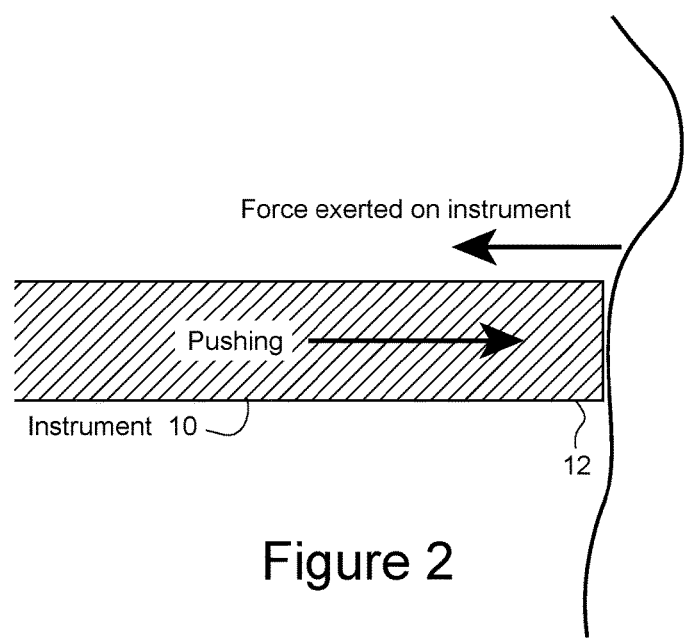
FIG. 2 is a diagram illustrating an example force exerted on an instrument.

FIG. 2 is a diagram illustrating an example force exerted on an instrument 10. Referring to the robotic medical example in FIG. 1, the force on the instrument 10 may be due to the distal region of pushing on tissue or some other structure which likely causes the instrument distal region to compress. Reference numeral 12 indicates a distal region of the instrument 10.

Figure 3:
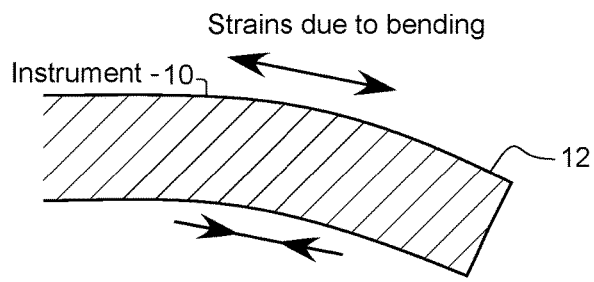
FIG. 3 is a diagram illustrating example strains on an instrument.

FIG. 3 is a diagram illustrating example strains on an instrument 10. The inventors recognized that sensing strain at the distal region of the instrument 10 can be used to determine what loads or forces are applied to the distal region. It is often advantageous to determine the loads or forces at the distal region of an instrument. For example, in a medical application, it may be advantageous to know how much force is being applied to tissue by a catheter or other medical instrument, e.g., to avoid puncturing the tissue and/or to provide feedback to the instrument operator.

Figure 4:
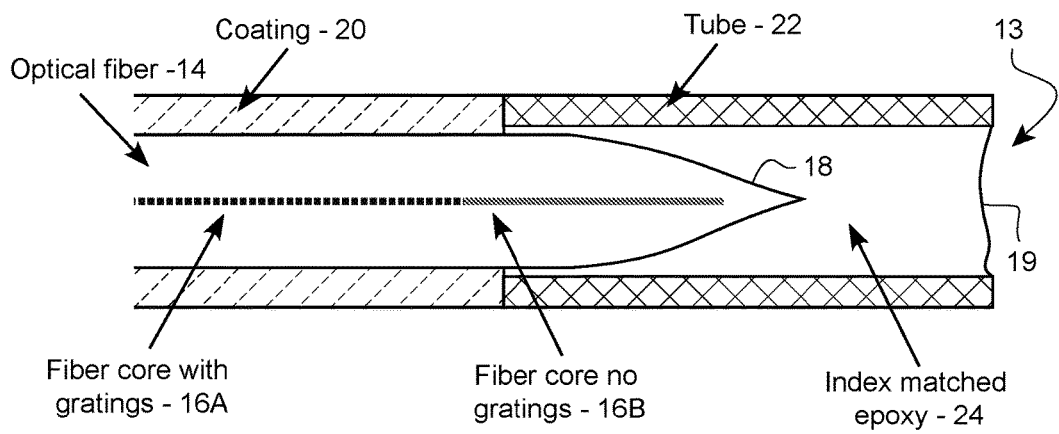
FIG. 4 shows a non-limiting example embodiment of an optical fiber structure for use in an instrument.

FIG. 4 shows a non-limiting example embodiment of an optical fiber structure for use in an instrument 10. An optical fiber 14 includes an optical core 16 surrounded by a cladding, which is protected by a surrounding coating 20. A tapered end of the fiber 18 is encased in a protective tube 22 or similar structure and secured therein using any suitable securing mechanism. The tube 22 may be made of metal, glass, or polymer and completely surrounds the end of the optical fiber 18. In an example embodiment, the core is secured using an index-matched epoxy 24. The epoxy 24 transfers strain from the tube to the optical fiber. Reference numeral 19 indicates a distal end of the epoxy within the tube 22. The fiber core shown in FIG. 4 includes Bragg gratings 16A, but those gratings are not present in a portion of the core 16B encased in the tube 22. Reference numeral 13 generally refers to a distal region of the optical fiber 14.

Figure 5:
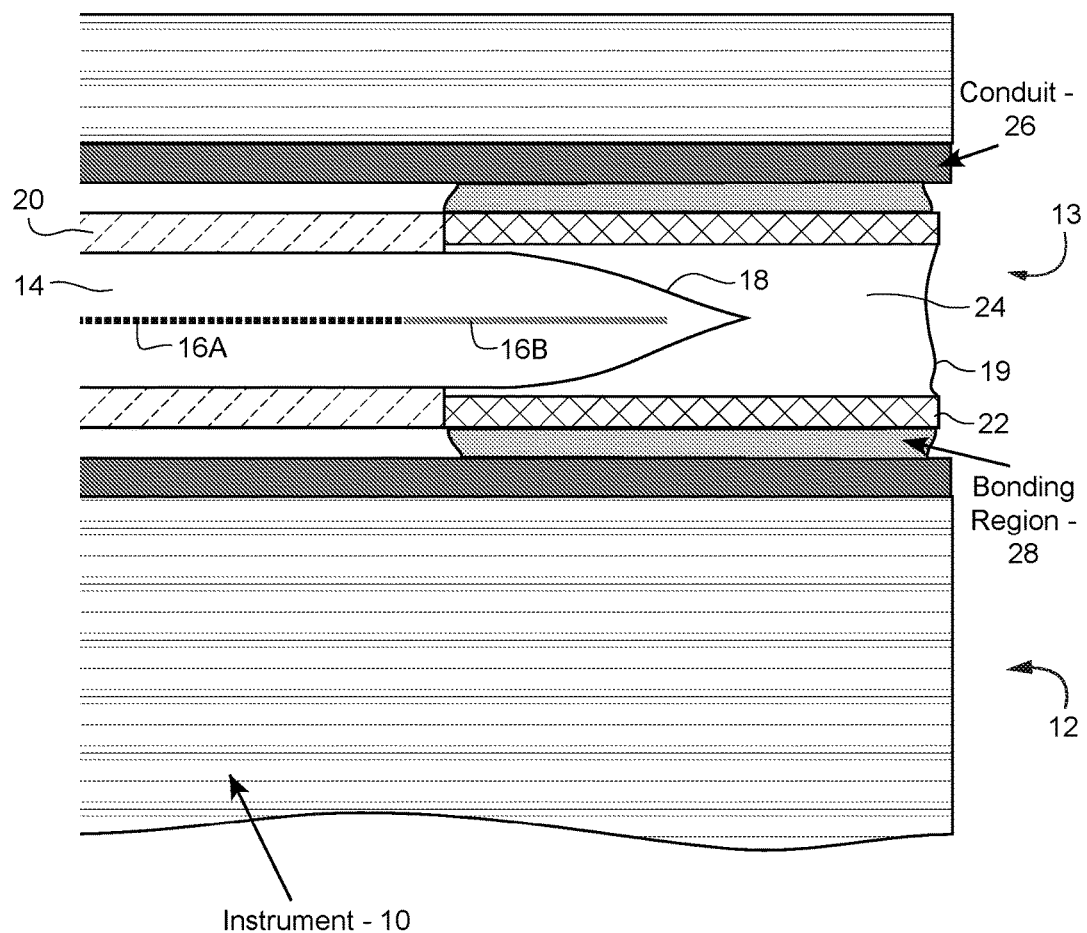
FIG. 5 illustrates a non-limiting example embodiment of an end of an instrument including the optical fiber structure shown in FIG. 4.

FIG. 5 illustrates a non-limiting example embodiment of a distal region (indicated generally at 12) of an instrument 10 including the optical fiber structure shown in FIG. 4. The optical fiber 14 and metal tube 22 protecting the end of the fiber 18 is inserted into a conduit 26 in the instrument 10 and secured to at the end of the instrument. For example, the tube 22 may be mechanically bound to the instrument at the end of the instrument 12 via a bonding region 28. This bond transfers the strain experienced at the end 12 of the instrument 10 to the end 13 of the fiber 14. Example securing mechanisms other than mechanical attachment include securing the tube 22 to the conduit 26 at the end of the optical fiber using an adhesive attachment or a flame spray attachment.

FIGS. 6A-6C show various views of the end of the instrument shown in FIG. 5. FIG. 6A shows a cross-section of the instrument having multiple conduits, with conduits 26a and 26b being examples of conduits in which optical fiber sensors are inserted. FIG. 6b shows a side view following the cross-section line 6B-6B shown in FIG. 6A. FIG. 6C shows an enlarged portion of an end of one conduit 26A identified by the dashed circle in FIG. 6B.

Figure 7:
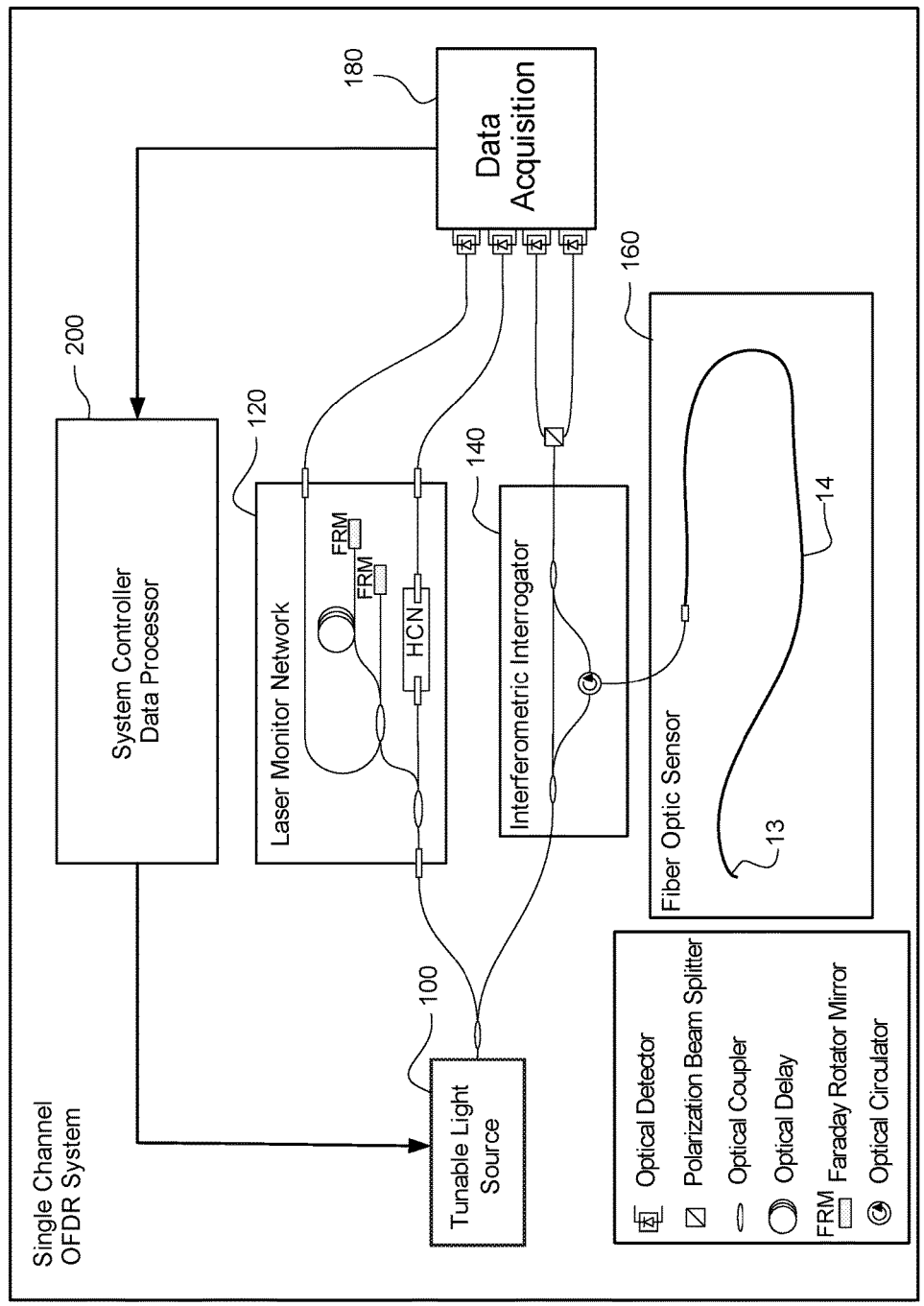
FIG. 7 shows a non-limiting example embodiment using an OFDR-based, single core fiber force sensing system.

FIG. 7 shows a non-limiting example embodiment using an OFDR-based, single core fiber force sensing system for use an instrument 10 including an optical fiber 14 having a distal region 13 such as that shown in FIG. 5. The optical fiber in the instrument is connected to an Optical Frequency Domain Reflectometry (OFDR) system which is an example of an optical interferometric interrogation system. A continuous measure of strain along the length of a core can be derived by interpreting the optical response of the core using swept wavelength inteferometery. Optical time domain measurements with high resolution and high sensitivity may be achieved using OFDR. The single channel OFDR system (a single channel is used to interrogate a single optical fiber core) includes a tunable light source 100, an interferometric interrogator 140, a laser monitor network 120, data acquisition electronic circuitry 180, and a system controller data processor 200.

Figure 8:
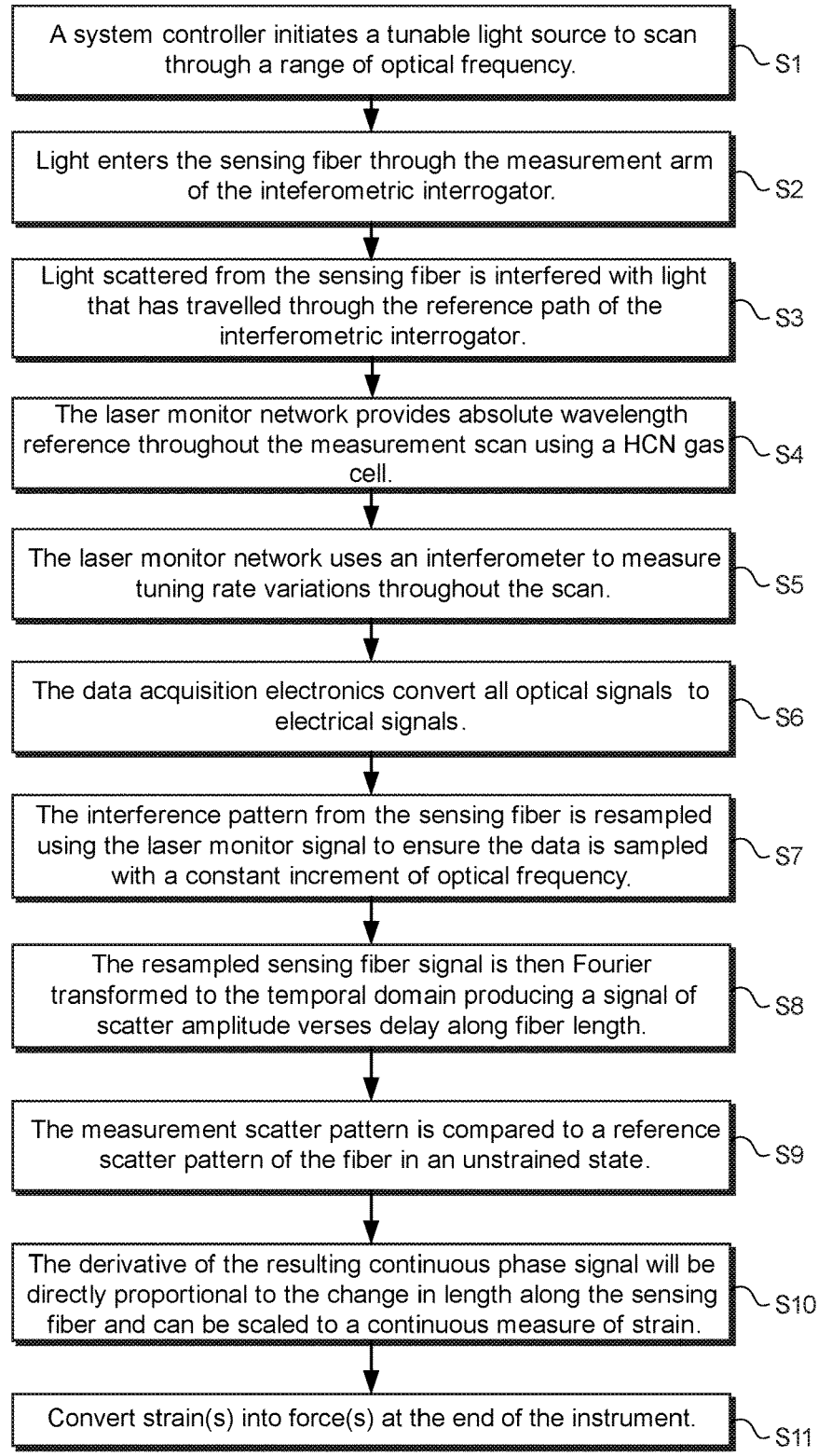
FIG. 8 is a flowchart illustrating example procedures for interferometrically-based single core fiber force sensing using the example system in FIG. 7.

FIG. 8 is a flowchart illustrating example procedures for interferometrically-based single core fiber force sensing using the example system in FIG. 7. The steps describe the operation for one core. For the multicore example embodiment described below, these steps are applied to each of the cores.

During an OFDR measurement, a tunable light source 23 is swept through a range of optical frequencies (step S1). This light is split with the use of optical couplers and routed to two separate interferometers 26 and 28. The first interferometer 26 serves as an interferometric interrogator and is connected via a connector 24 to a length of sensing fiber. Light enters the multicore sensing fiber 10 through the measurement arm of the interferometric interrogator 26 (step S2). Scattered light from the sensing fiber 14 is then interfered with light that has traveled along the reference arm of the interferometric interrogator 26 (step S3). The laser monitor network 28 contains a Hydrogen Cyanide (HCN) gas cell that provides an absolute wavelength reference throughout the measurement scan (step S4). The second interferometer, within the laser monitor network 28, is used to measure fluctuations in tuning rate as the light source is scanned through a frequency range (step S5). A series of optical detectors (e.g., photodiodes) convert the light signals from the laser monitor network, gas cell, and the interference pattern from the sensing fiber to electrical signals (step S6). A data processor in a data acquisition unit 32 uses the information from the laser monitor 28 interferometer to resample the detected interference pattern of the sensing fiber 14 so that the pattern possesses increments constant in optical frequency (step S7). This step is a mathematical requisite of the Fourier transform operation. Once resampled, a Fourier transform is performed by the system controller 30 to produce a light scatter signal in the temporal domain for an initial orientation of the single core fiber 14 (step S8). In the temporal domain, the amplitudes of the light scattering events are depicted verses delay along the length of the fiber. Using the distance that light travels in a given increment of time, this delay can be converted to a measure of length along the sensing fiber. In other words, the light scatter signal indicates each scattering event as a function of distance along the fiber. The sampling period is referred to as the spatial resolution and is inversely proportional to the frequency range that the tunable light source 100 was swept through during the measurement.

As the fiber is strained, the local light scatters shift as the fiber changes in physical length. These distortions are highly repeatable. Hence, an OFDR measurement of detected light scatter for the fiber can be retained in memory that serves as a reference pattern of the fiber in an unstrained state. A subsequently measured scatter signal when the fiber is under strain may then be compared to this reference pattern by the system controller 200 to gain a measure of shift in delay of the local scatters along the length of the sensing fiber (step S9). This shift in delay manifests as a continuous, slowly varying optical phase signal when compared against the reference scatter pattern. The derivative of this optical phase signal is directly proportional to change in physical length of the sensing core (step S10). Change in physical length may be scaled to strain producing a continuous measurement of strain along the sensing fiber. The measured strain(s) are then converted into force(s) experienced at the end of the instrument (step S11).

Detected strain at the end of the instrument may be converted to force in accordance with the following. Young's modulus, E, may be calculated by dividing tensile stress by extensional strain in an elastic (initial, linear) portion of the stress-strain curve:

$$E \equiv \frac{\text{tensile stress}}{\text{extensional strain}} = \frac{\sigma}{\epsilon} = \frac{F/A_0}{\Delta L/L_0} = \frac{FL_0}{A_0 \Delta L}$$

where:
E is the Young's modulus (modulus of elasticity)
F is the force exerted on an object under tension;
$A_0$ is the original cross-sectional area through which the force is applied;
$\Delta L_0$ is the amount by which the length of the object changes; and
$L_0$ is the original length of the object.

The Young's modulus of a material can be used to calculate the force exerted on it under specific strain:

$$F = \frac{EA_0 \Delta L}{L_0}$$

where F is the force exerted on the material when contracted or stretched by $\Delta L$. This equation can be simplified to $F = E*A_0*\epsilon$, where E may be the Young's modulus for and $A_0$ may be the cross sectional area of the distal region of the instrument 12.

In some cases, the structural contribution of the optical fiber to the instrument may be ignored. On the other hand, as the stiffness of the fiber becomes a significant portion of the stiffness of the instrument, the fiber is preferably considered as part of the cross sectional area and modulus. In this latter situation, which may be the case for many medical instruments, $A_0$ is taken as the entire cross sectional area of the structure including the fiber and an effective E is modeled analytically for the combined components that make up the distal region structure of the instrument. Another alternative is to calibrate the system with a series of known loads. In this approach, a series of known loads is applied to the instrument, and the strain at the end of the fiber is measured for each load. A proportionality constant or curve is then determined relating strain on the fiber to load applied to the instrument. In effect, this proportionality constant or curve is a measure of $A_0 E$.

Ultimately, the system controller 200 calculates the a at the distal region of the instrument as described above, and the force(s) at the distal region of the instrument using the $F = E*A_0*\epsilon$ and the determined values for $A_0$ and E.

Figure 9A:
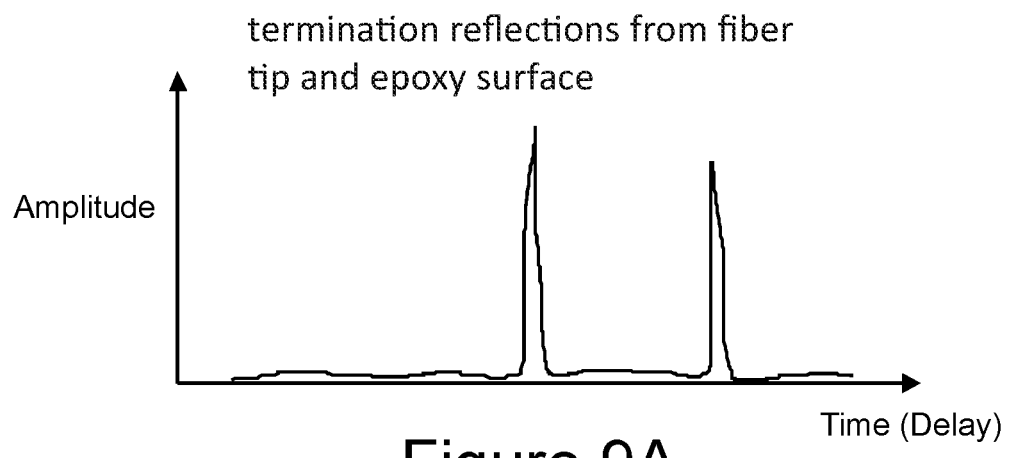
FIG. 9A shows a non-limiting example graph of detected reflections from the distal region of the instrument.

FIG. 9A shows a non-limiting example graph of detected reflections from the distal region of the sensor. Using OFDR, these reflections appear as two distinct peaks in the time domain plot of reflection vs. distance. The first detected reflection is from the distal region of the instrument 12, and the second detected reflection is from the terminating surface 19 of the epoxy 24 as shown in FIG. 5. As strain is applied to the distal region of the instrument 12, the distance between these peaks changes.

Figure 9B:
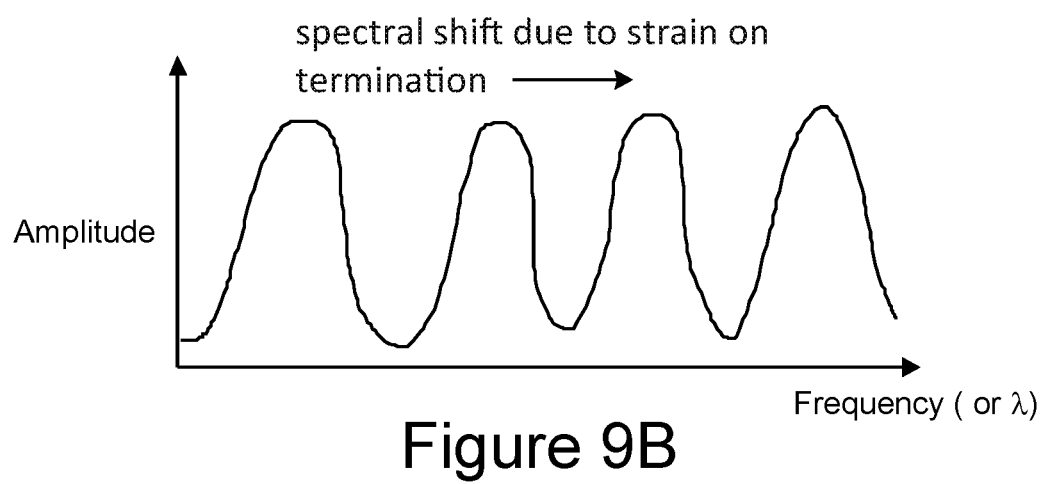
FIG. 9B shows a non-limiting example graph of detected strain based on the reflections from the distal region of the instrument shown in FIG. 10A.

FIG. 9B shows a non-limiting example graph of the reflected spectrum at the distal region of the sensor based on the reflections from the distal region of the sensor shown in FIG. 9A. In the spectral domain, these two reflections form an interference pattern with a sinusoidal oscillation as a function of optical frequency. The period of this oscillation is determined by the separation between the peaks. Therefore, measuring the change in the period of this spectral interference provides a measure of the strain at the end of the instrument 12. This process applies if there are two or more reflections in the distal region structure. Each strain measure is converted to a force at the distal region of the instrument 12 using the conversion described above.

More minute reflections are caused by scattering in the fiber at the distal region. As can be seen in FIG. 5, within the tube 22, light travels through a small section of fiber that includes Bragg gratings, then passes through a length of fiber where the heat from a fiber tapering process has erased the Bragg gratings, and then exits the fiber core altogether. In one example embodiment a measure of the force present on the tube 22 is obtained by measuring the scattering events within the tube and noting the changes that occur. Strain is determined by examining the cross correlation of the spectral amplitude of the scatter pattern obtained for the distal region in an unstrained reference state and the scatter pattern detected for the distal region in a strained state.

Figure 10:
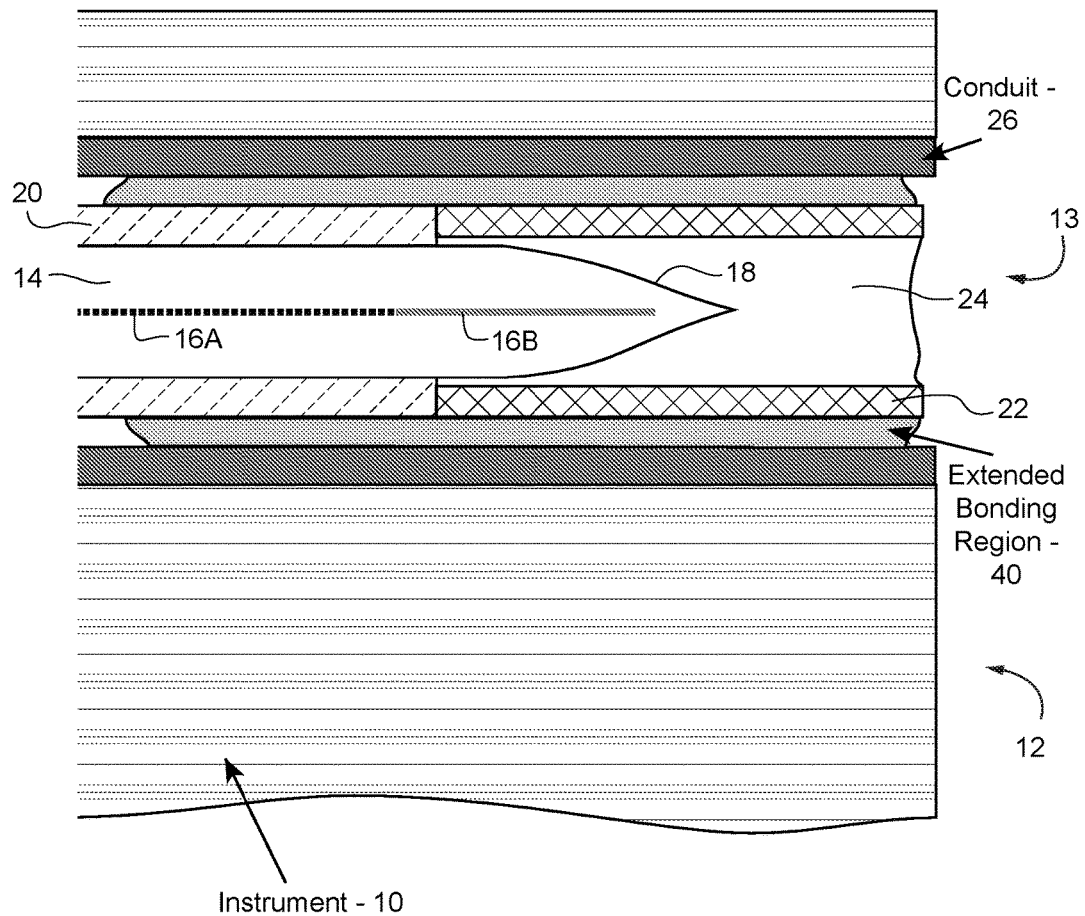
FIG. 10 illustrates another non-limiting example embodiment of an end of an instrument including the optical fiber structure shown in FIG. 4.

FIG. 10 illustrates another non-limiting example embodiment of an end of a fiber optic instrument 10 including the optical fiber structure shown in FIG. 4. The bonding region is extended such that some Bragg gratings within the fiber core at region 16A are present within the bonded region 40. The spectral shifts or phase derivatives of the reflections determined from these gratings may be used to determine the strain at the distal region.

For all of these embodiments, either single-core or multi-core fibers may be used. The selection would likely be determined by what is most convenient to the application. If multi-core fiber is already present for shape sensing, for example, then it may be most convenient to use the already present sensor. If not, then a single core fiber could be a less expensive and simpler to use option.

Figure 11:
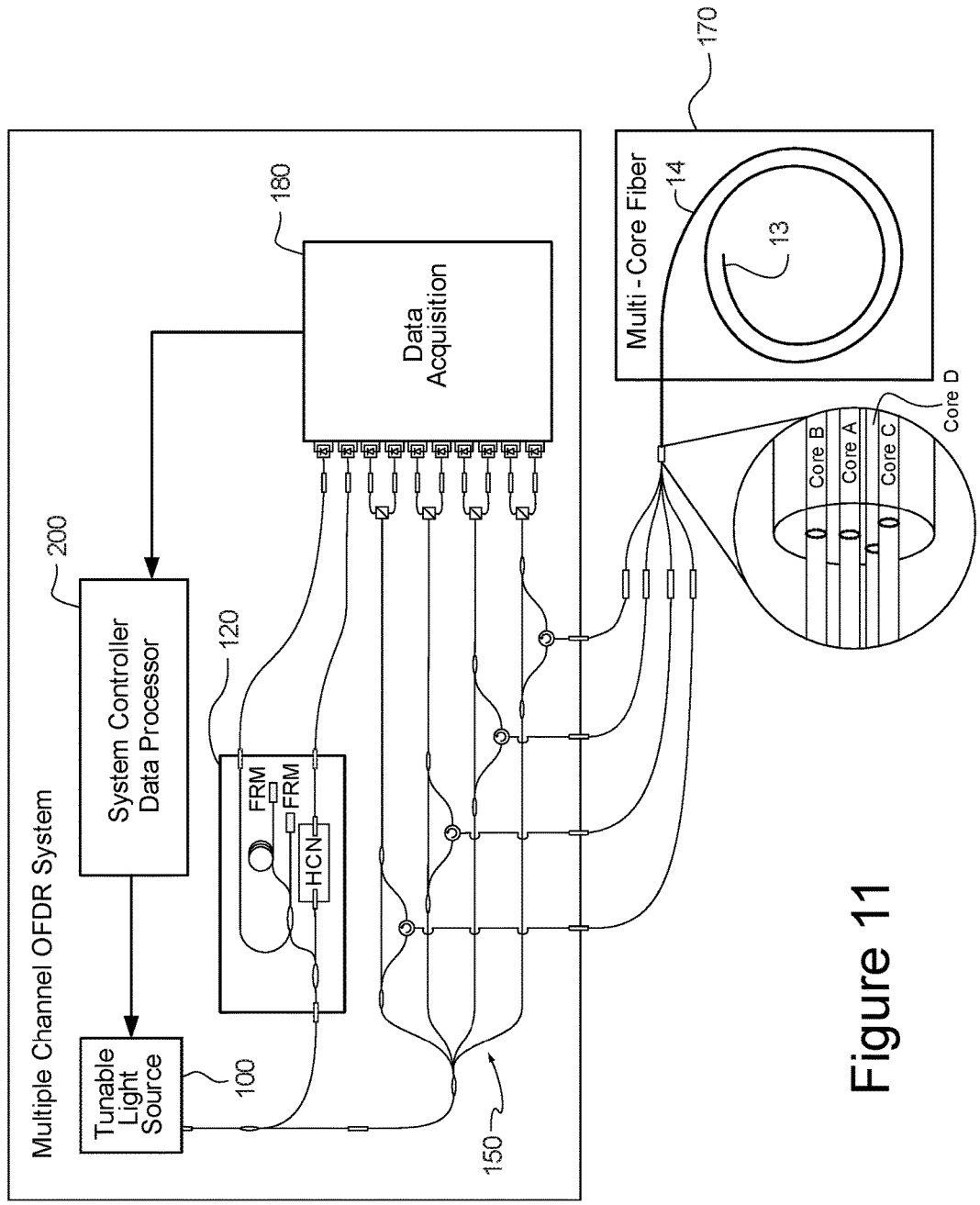
FIG. 11 shows a non-limiting example embodiment using an OFDR-based, multiple core fiber force sensing system.

FIG. 11 shows a non-limiting example embodiment using a multiple channel OFDR, multiple core fiber force sensing system. This system is similar to that shown in FIG. 7 except that the fiber includes multiple cores, i.e. a multi-core fiber 170. Four examples cores are shown A-D. Similar procedures may be carried out for each core as shown in FIG. 8 described above. In the case of multi-core fiber, bending at the distal region 13 causes different strains in the outer cores of the fiber, whereas axial strain results in common mode strain in all the cores of the fiber. This difference can be used to distinguish between strain due to bending and axial strains due to, for example, pushing on tissue. This eliminates the need for a second sensor to distinguish between these different causes of strain at the distal region 13.

For multi-core fiber with multiple cores terminating into the same tube 22, there is the possibility that the signals from each core will be mixed together within the tube 22 which may adversely impact accurate reflection signal detection. Therefore, it may be desirable to interrogate the multicore fiber sensor in this case with at least one of the cores being offset in interferometric path length to prevent interaction with the light from the other cores. See, for example, commonly-assigned, U.S. patent application Ser. No. 13/113,761, filed on May 23, 2011, and entitled "Interferometric Measurement with Crosstalk Suppression." This is done by changing the fiber lengths in the interferometric interrogator (e.g., OFDR) such that they do not match for different cores in the multi-core sensor. For example, in FIG. 11, the reference or measurement path for each fiber core is altered so they are not the same as that of another fiber core. This offsets the apparent location in the time domain of the reflections from the distal region of the sensor for each core. One example offset is more than the length over which the reflections from the distal region occur.

As described above, bending forces can cause strain at the end of the instrument in addition to strains due to pushing on tissue or some other structure. It may be desirable to distinguish these two sources of strain. One example way to do this uses two (or more) sensors, e.g., each on opposite sides of the instrument. This is illustrated in FIG. 6B showing two fibers in two conduits 26A and 26B in the instrument. If the instrument is bent in the plane containing the two fiber sensors, one fiber sensor would experience compression and the other tension in equal but opposite magnitudes. The common mode strain would be the remaining strain due to force applied by the instrument distal region to some structure, e.g., tissue for a medical instrument like that shown in FIG. 1. This method is directed to single core fiber embodiments. As described above, using a multicore fiber allows for distinguishing bending from pushing with a single sensor.

To measure strains in the second sensor, two OFDR systems may be used, or a network and acquisition hardware may be used to measure all the desired cores in the two sensors. Optical splitters in the network, as shown in FIG. 12, may be used to accommodate multiple cores and more detection channels can be added to the acquisition hardware to accommodate more signals.

Although various embodiments have been shown and described in detail, the claims are not limited to any particular embodiment or example. None of the above description should be read as implying that any particular element, step, range, or function is essential such that it must be included in the claims scope. The scope of patented subject matter is defined only by the claims. The extent of legal protection is defined by the words recited in the allowed claims and their equivalents. All structural and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the technology described, for it to be encompassed by the present claims. No claim is intended to invoke paragraph 6 of 35 USC § 112 unless the words "means for" or "step for" are used. Furthermore, no embodiment, feature, component, or step in this specification is intended to be dedicated to the public regardless of whether the embodiment, feature, component, or step is recited in the claims.

The invention claimed is:

1. An optical force sensor, comprising:
   an optical fiber having a length;
   a core included in the optical fiber, wherein the core includes a plurality of Bragg gratings along an entire length of the optical fiber except for a portion of the core corresponding to an end region of the optical fiber where no Bragg gratings exist;
   an instrument including the optical fiber, the instrument having a distal region and a proximal region;
   a tubular structure encasing the end region of the optical fiber where no Bragg gratings exist and secured at the distal region of the instrument;
   the optical fiber being configured for connection to an optical interferometric system which processes reflected light corresponding to a Rayleigh scatter pattern distributed along a portion of the core included within the tubular structure that does not include Bragg gratings to produce a measurement of strain due to a force present at the distal region of the instrument separate from bending induced strain.

2. The optical force sensor in claim 1, wherein the optical fiber is tapered within the tubular structure and is secured within the tubular structure by an epoxy index-matched to the optical fiber.

3. The optical force sensor in claim 2, wherein the epoxy transfers strain from the distal region of the instrument to the optical fiber.

4. The optical force sensor in claim 1, wherein the tubular structure is made of metal, glass, or polymer and completely surrounds the end of the optical fiber.

5. The optical force sensor in claim 1, wherein the tubular structure is secured at the end of the optical fiber using a mechanical attachment, an adhesive attachment, or a flame spray attachment.

6. The optical force sensor in claim 1, wherein the instrument includes a first conduit into which the optical fiber is inserted, and wherein the tubular structure is bonded to the first conduit at a bonded region that extends as far as the tubular structure, and wherein the core includes Bragg gratings except on a portion of the core defined by the bonded region.

7. The optical force sensor in claim 1, wherein the instrument includes a first conduit into which the optical fiber is inserted, and wherein the tubular structure is bonded to the first conduit at the end of the optical fiber at a bonded region that extends beyond the tubular structure and secures the optical fiber to the first conduit, and wherein the core includes Bragg gratings that extend into the bonded region.

8. The optical force sensor in claim 1, wherein the optical fiber includes multiple cores.

9. The optical force sensor in claim 1, wherein the instrument includes a first conduit into which the optical fiber is inserted and a second conduit containing another optical fiber encased in a tubular structure like the optical fiber and tubular structure recited in claim 1, and wherein the optical interferometric system processes reflected light from portions of the core contained within the tubular structures of the respective optical fibers that do not include Bragg gratings to produce a measurement of forces present on the respective tubular structures.

10. An optical processing apparatus, comprising:
    an optical fiber having a length;
    a core included in the optical fiber, wherein the core includes a plurality of Bragg gratings along an entire length of the optical fiber except for a portion of the core corresponding to an end region of the optical fiber where no Bragg gratings exist;
an instrument including the optical fiber, the instrument having a distal region and a proximal region;
a tubular structure encasing the end region of the optical fiber where no Bragg gratings exist and secured at the distal region of the instrument;
an optical interferometric system coupled to the optical fiber and configured to process reflected light corresponding to a Rayleigh scatter pattern distributed along a portion of the core included within the tubular structure that does not include Bragg gratings to produce a measurement of strain due to a force present at the distal region of the instrument separate from bending induced strain.

11. The optical processing apparatus in claim 10, wherein the optical fiber is tapered within the tubular structure and is secured within the tubular structure by an epoxy index-matched to the optical fiber, the epoxy transferring strain from the instrument to the optical fiber.

12. The optical processing apparatus in claim 11, wherein the optical interferometric system is configured to determine strain present on the distal region of the instrument and to determine the force based on the determined strain.

13. An optical processing apparatus, comprising:
an optical fiber having a length;
a core included in the optical fiber, wherein the core includes a plurality of Bragg gratings along an entire length of the optical fiber except for a portion of the core corresponding to an end region of the optical fiber where no Bragg gratings exist;
an instrument including the optical fiber, the instrument having a distal region and a proximal region;
a tubular structure encasing the end region of the optical fiber where no Bragg gratings exist and secured at the distal region of the instrument;
an optical interferometric system coupled to the optical fiber and configured to process reflected light from a portion of the core included within the tubular structure that does not include Bragg gratings to produce a measurement of strain due to a force present at the distal region of the instrument separate from bending induced strain,
wherein the optical fiber is secured within the tubular structure by an epoxy, and
wherein the optical interferometric system is configured to determine the strain present on the distal region of the instrument based on a first light reflection from a distal end of the optical fiber and on a second light reflection from a distal end surface of the epoxy.

14. The optical processing apparatus in claim 13, wherein the first and second light reflections form an interference pattern with a sinusoidal oscillation as a function of optical frequency, and wherein the optical interferometric system is configured to measure a change in a period of the sinusoidal oscillation to determine the strain present on the distal region of the instrument.

15. The optical processing apparatus in claim 10, wherein the optical interferometric system is configured to detect the scatter pattern, compare the detected scatter pattern to a reference scatter pattern to determine a difference, and determine the force based on the difference.

16. The optical processing apparatus in claim 10, wherein the instrument includes a first conduit into which the optical fiber is inserted and a second conduit into which a second optical fiber is inserted and a second tubular structure encasing an end of the second optical fiber located at the distal region and secured within the second tubular structure by an epoxy index-m to the optical fiber, the epoxy transferring strain from the first and second conduits to the optical fiber, and wherein the optical interferometric system is configured to process reflected light from a portion of respective cores in the first and second optical fibers that do not include Bragg gratings to produce a measurement of multiple forces present on the distal region of the instrument.

17. An optical processing method using an optical fiber including a core attached to an instrument having a distal region, where a tubular structure encases an end of the optical fiber and is secured at the distal region of the instrument, the method comprising:
processing, using an optical interferometric system, a phase of reflected light from a portion of the core included within the tubular structure that does not include Bragg gratings to produce a measurement of a force present at the distal region of the instrument.

18. The optical processing method in claim 17, further comprising determining strain present on the distal region of the instrument and determining the force based on the determined strain.

19. The optical processing method in claim 18, wherein the optical interferometric system determines the strain present on the distal region of the instrument based on a first light reflection from a distal end of the optical fiber and on a second light reflection from a distal end surface of the epoxy,
wherein the first and second light reflections form an interference pattern with a sinusoidal oscillation as a function of optical frequency, and
wherein the method further comprises:
measuring a change in a period of the sinusoidal oscillation to determine the strain present on the distal region of the instrument.

20. The optical processing method in claim 17, further comprising:
detecting a scatter pattern within the tubular structure,
comparing the detected scatter pattern to a reference scatter pattern to determine a difference, and
determining the force based on the difference.

* * * * *